United States Patent
Geist et al.

(10) Patent No.: US 11,633,223 B2
(45) Date of Patent: Apr. 25, 2023

(54) SURGICAL GUIDANCE DEVICE

(71) Applicant: Integrity Implants Inc., Jupiter, FL (US)

(72) Inventors: Wyatt Drake Geist, Davie, FL (US); Jared M. White, West Palm Beach, FL (US)

(73) Assignee: INTEGRITY IMPLANTS INC., Palm Beach Gardens, FL (US)

( * ) Notice: Subject to any disclaimer, the term of this patent is extended or adjusted under 35 U.S.C. 154(b) by 328 days.

(21) Appl. No.: 16/848,299

(22) Filed: Apr. 14, 2020

(65) Prior Publication Data
US 2020/0305944 A1    Oct. 1, 2020

Related U.S. Application Data

(63) Continuation-in-part of application No. 16/722,944, filed on Dec. 20, 2019, now Pat. No. 11,344,353.
(Continued)

(51) Int. Cl.
*A61B 17/00*    (2006.01)
*A61B 17/70*    (2006.01)
(Continued)

(52) U.S. Cl.
CPC ...... *A61B 17/8897* (2013.01); *A61B 17/7001* (2013.01); *A61B 17/7091* (2013.01);
(Continued)

(58) Field of Classification Search
CPC ............ A61B 17/7082; A61B 17/7092; A61B 17/848; A61B 17/8861
See application file for complete search history.

(56) References Cited

U.S. PATENT DOCUMENTS 2,243,717 A    5/1941  Moreira
2,291,413 A    7/1942  Siebrandt
(Continued)

OTHER PUBLICATIONS

Anonymous, Alfa Tech, Retrieved from Internet Mar. 19, 2020, https://linkedin.com/posts/alfatec-spine_atec-organic-innovation-machine-activity-6628772455886528512-gm5n/.
(Continued)

*Primary Examiner* — Nicholas W Woodall
(74) *Attorney, Agent, or Firm* — McHale & Slavin, P.A.

(57) ABSTRACT

Briefly, the invention relates to a surgical tool and method for forming a pilot bore by inserting a guide wire into bone. The surgical tool is constructed and arranged for use in conjunction with X-ray or ultrasound machines. More particularly, the device includes a cannulated hand grip and driving tool used for the rotation of a bone or pedicle screw into bone. The rear portion of the hand grip includes a slide assembly that is suited to grip a guide wire. The slide assembly includes a user adjustable stop to control the sliding movement of the guide wire. The rear surface of the slide is constructed to be impacted with a hammer or similar device, whereby the stop prevents the guide wire from penetrating the bone further than desired. Should it be desired that the wire be retracted, a jack member is included to allow the wire to be precisely retracted. The hand grip is securable to various surgical driving tools for the purpose of providing the ability to cooperate with various brands of pedicle screws and other surgical implants for spinal procedures.

13 Claims, 5 Drawing Sheets

Related U.S. Application Data

(60) Provisional application No. 62/783,054, filed on Dec. 20, 2018.

(51) Int. Cl.
*A61B 17/84* (2006.01)
*A61B 17/88* (2006.01)
*A61B 90/00* (2016.01)

(52) U.S. Cl.
CPC . *A61B 2017/0042* (2013.01); *A61B 2090/062* (2016.02); *A61B 2090/376* (2016.02); *A61B 2090/378* (2016.02); *A61B 2090/3764* (2016.02)

(56) References Cited

U.S. PATENT DOCUMENTS

| | | | |
|---|---|---|---|
| 3,351,054 A | 11/1967 | Florek | |
| 4,638,799 A * | 1/1987 | Moore | A61B 17/3478 606/76 |
| 5,139,500 A | 8/1992 | Schwartz | |
| 7,207,995 B1 * | 4/2007 | Vandewalle | A61B 17/8875 606/104 |
| 9,254,160 B2 * | 2/2016 | Pakzaban | A61B 17/8875 |
| 9,956,021 B1 | 5/2018 | Aebi et al. | |
| 10,433,883 B2 | 10/2019 | DiVincenzo et al. | |
| 10,779,872 B2 | 9/2020 | Smith et al. | |
| 10,973,558 B2 | 4/2021 | Kam et al. | |
| 2005/0033393 A1 * | 2/2005 | Daglow | A61B 17/3415 607/116 |
| 2008/0004214 A1 * | 1/2008 | Trieu | A61K 31/728 514/8.8 |
| 2009/0275954 A1 | 11/2009 | Phan et al. | |
| 2011/0054537 A1 | 3/2011 | Miller et al. | |
| 2012/0004665 A1 | 1/2012 | Defossez et al. | |
| 2014/0039534 A1 | 2/2014 | Geist et al. | |
| 2014/0094822 A1 | 4/2014 | Baynham | |
| 2015/0201985 A1 * | 7/2015 | Rampersaud | A61B 17/7082 606/86 A |
| 2016/0030100 A1 | 2/2016 | Divicenzo et al. | |
| 2018/0064473 A1 | 3/2018 | Karadeniz | |
| 2018/0132920 A1 | 5/2018 | Vikinsky et al. | |
| 2019/0262055 A1 | 8/2019 | Haziza | |
| 2020/0093530 A1 | 3/2020 | Klausman et al. | |
| 2020/0197064 A1 | 6/2020 | Geist et al. | |
| 2020/0305944 A1 | 10/2020 | Geist et al. | |
| 2020/0323566 A1 | 10/2020 | Geist et al. | |
| 2020/0390486 A1 | 12/2020 | Rodriguez et al. | |
| 2021/0161571 A1 | 6/2021 | Haziza | |

OTHER PUBLICATIONS

Anonymous, Dupuy Spine, Retrieved from Internet Mar. 19, 2020, https://vimeo.com/260201759/.

Anonymous, Astura Spine, Retrieved from Internet Mar. 19, 2020, https://asturamedical.com/product/olympic-mis/.

* cited by examiner

SURGICAL GUIDANCE DEVICE

RELATED APPLICATIONS

In accordance with 37 C.F.R. § 1.76, a claim of priority is included in an Application Data Sheet filed concurrently herewith. Accordingly, this present invention claims priority as a continuation in part of U.S. patent application Ser. No. 16/722,944, entitled "SURGICAL GUIDANCE DEVICE AND SYSTEM FOR INSERTION THEREOF" filed Dec. 20, 2019, which claims priority of U.S. Provisional Application No. 62/783,054, entitled "SURGICAL GUIDANCE DEVICE AND SYSTEM FOR INSERTION THEREOF" filed Dec. 20, 2018, the contents of which are incorporated herein by reference.

FIELD OF THE INVENTION

The invention relates to a guidance instrument and a device for insertion of the guidance instrument for surgical spinal procedures. In particular, the device includes a driving tool for inserting and positioning a guide wire into bone in addition to a tool for inserting a pedicle screw into a vertebra.

BACKGROUND

Medical procedures involving the vertebrae are normally complicated because of the preciseness and accuracy required to avoid both neural damage and injury to major blood vessels. Precision depth guided instruments are required to perform percutaneous spinal surgery. These surgeries sometimes require penetration of the hard cortical bone of the vertebra and traversal of the softer cancellous bone lying thereunder. A large force is normally required by the surgeon to penetrate the cortical bone. Once the cortical bone is penetrated, extreme care must then be taken to avoid rapidly penetrating through all of the cancellous bone. There is also the danger of rapidly passing through the cancellous bone and then through the cortical bone on the other side of the vertebra. This can result in injury or damage to the spinal cord and/or other organs or blood vessels located adjacent the spine. In some instances, the force required to penetrate the cortical bone is greater than a surgeon can apply by hand. In these instances, a hammer or other similar instrument is required to force the instrument through the cortical bone. When a hammer or similar instrument is used, there is a greater danger of the instrument passing rapidly through the cancellous bone and out the other side of the vertebra.

Thus, what is needed is a device and method for inserting a small diameter guide wire that is capable of precisely controlling the depth that the guide wire can penetrate. The device and method should also be constructed to allow the user to precisely retract the guide wire through bone as needed.

SUMMARY

Briefly, the invention relates to a surgical tool and method for forming a pilot bore by inserting a guide wire into bone. The surgical tool is constructed and arranged for use in conjunction with X-ray or ultrasound machines. More particularly, the device includes a cannulated hand grip and driving tool used for the rotation of a pedicle screw into bone. The rear portion of the hand grip includes a slide assembly that is suited to grip a guide wire. The slide assembly cooperates with a user adjustable stop to control the sliding movement of the guide wire. The rear surface of the slide is constructed to be impacted with a hammer or similar device, whereby the stop prevents the guide wire from penetrating the bone further than desired. Should it be desired that the wire be retracted, a screw thread is included as part of the user adjustable stop to allow the wire to be precisely retracted. The hand grip is securable to various surgical driving tools for the purpose of providing the ability to cooperate with various brands of pedicle screws and other surgical implants for spinal procedures. Thus, more than one driving tool may be secured to the same surgical tool, and the driving tool is rotatable about the longitudinal axis of the surgical tool. This construction saves the surgeon time by forming the pilot bore, which may retain the guide wire. Since the pedicle screw is already positioned on the guide wire, the surgeon need only rotate the tool to insert the screw along the guide wire to its desired position. Once the screw is placed, the screw jack can be utilized to retract the guide wire.

Accordingly, it is an objective of the present invention to provide a surgical tool which can be utilized to provide a precise trajectory and insertion depth for a guide wire.

It is another objective of the present invention to provide a surgical tool for insertion of guide wires which can be secured to various drive tools for the insertion of a pedicle screw into a patient.

It is yet another objective of the present invention to provide a surgical tool for the insertion of a guide wire that includes a screw jack for retracting or removing a guide wire.

Still yet another objective of the present invention is to provide a surgical tool for formation of a pilot bore by insertion of a guide wire that includes a driving surface for a striking instrument and a stop for controlling the driving depth.

Still yet a further objective of the present invention is to provide a surgical tool that can be used to ensure a desired trajectory and/or depth of a pilot hole by advancing a guide wire or biopsy needle in any number of surgical procedures, such as bone marrow biopsies, placement of spinal implants, spinal surgery, including ensuring proper placement of pedicle screws during pedicle fixation procedures and ensuring proper trajectory during the establishment of an operative corridor to a target site.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Figure 1:
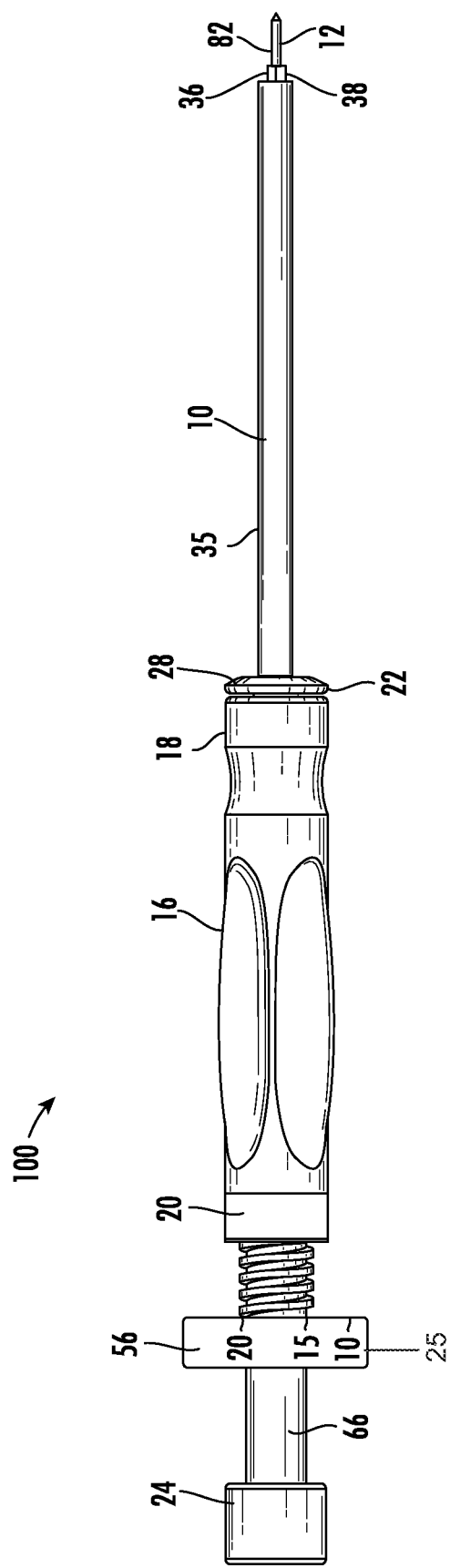
FIG. 1 is a side view of one embodiment of the surgical tool, illustrated with a guide wire and a driving tool for a pedicle screw.
Figure 2:
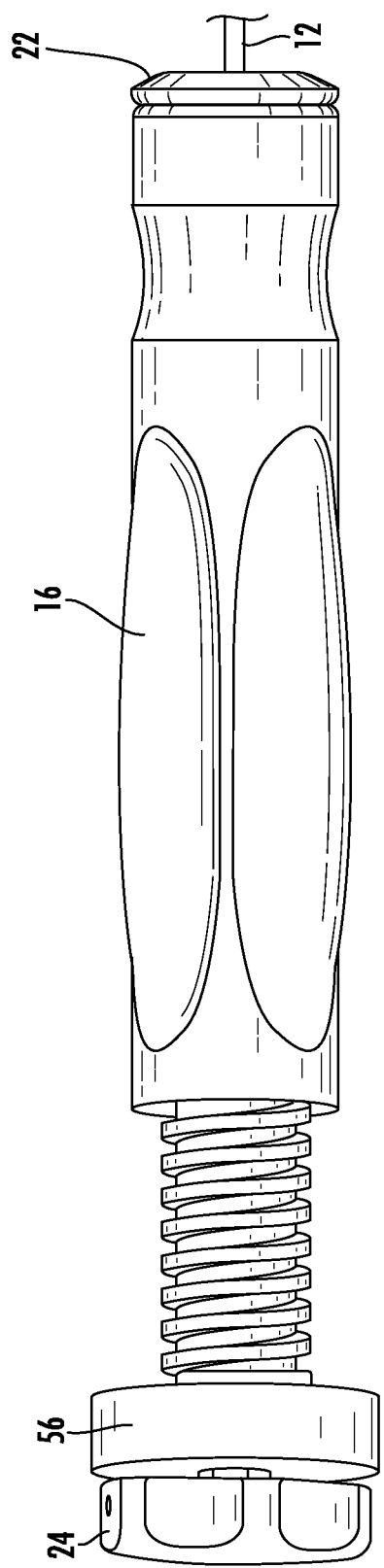
FIG. 2 is a partial perspective side view of the embodiment illustrated FIG. 1.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Various embodiments and surgical uses of devices are described for enhancing the safety and efficiency of surgical procedures. In one example, set forth by way of example only, the present invention may facilitate safe and reproducible pedicle screw guidance and placement by controlling the axial trajectory of a guide wire for pilot hole formation and/or screw insertion. In another example, set forth by way of example only, intraoperative imaging performance may be improved, and radiation exposure minimized, by providing precise control to the surgeon during guide wire depth placement. In yet another example, controlling the trajectory and depth of surgical access instruments can aid in both the insertion and positioning of the access instruments themselves, as well as aiding in the later insertion of instruments and/or implants through or with the surgical access instruments. It is expressly noted that these examples are set forth by way of example, and that the present invention may be suitable for use in any number of additional surgical actions where the angular orientation, trajectory or depth (linear distance traveled) of instrumentation and/or implants is important. By way of example only, the present invention may be useful in directing, among other things, the formation of tunnels for ligament or tendon repair and the placement of facet screws. Another example would include bone biopsies and the like. Other uses may include orientation of drills, saws, cutters or other hand operated tools used in the performance of surgery where specific fiducial markers may be useful.

Figure 3:
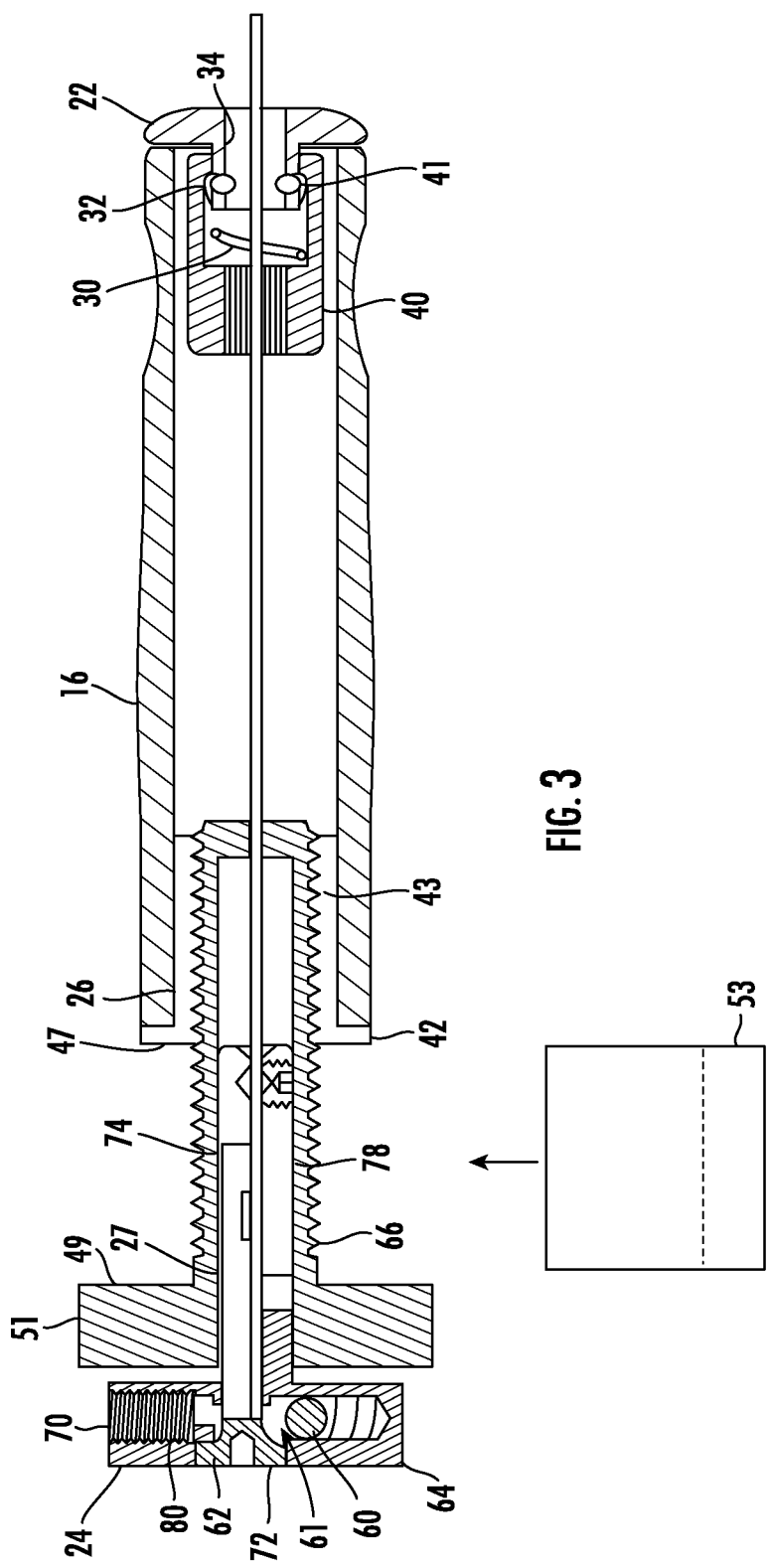
FIG. 3 is a section view taken along lines 3-3 of FIG. 4.
Figure 4:
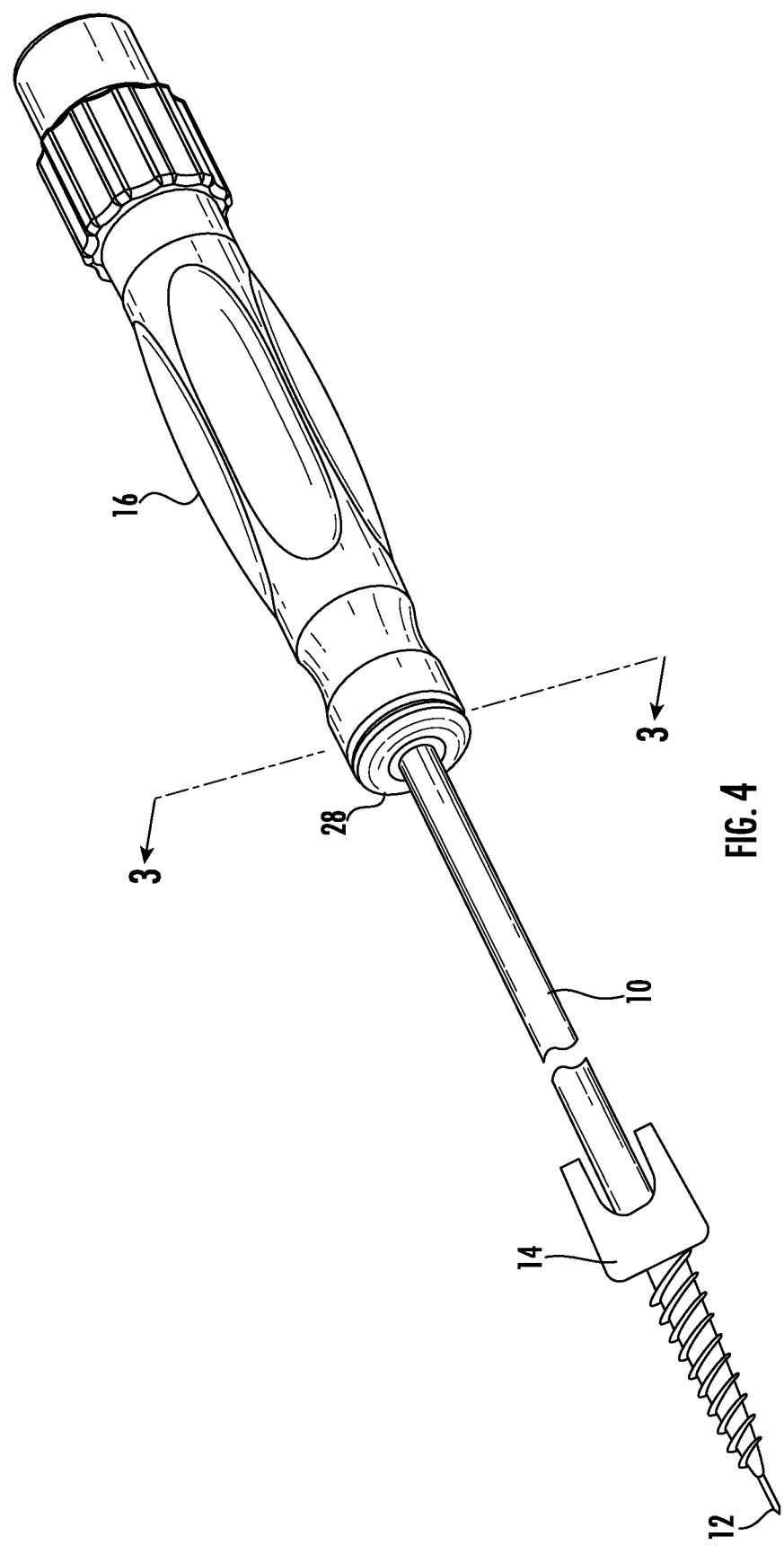
FIG. 4 is a perspective view of one embodiment of the surgical tool.
Figure 5:
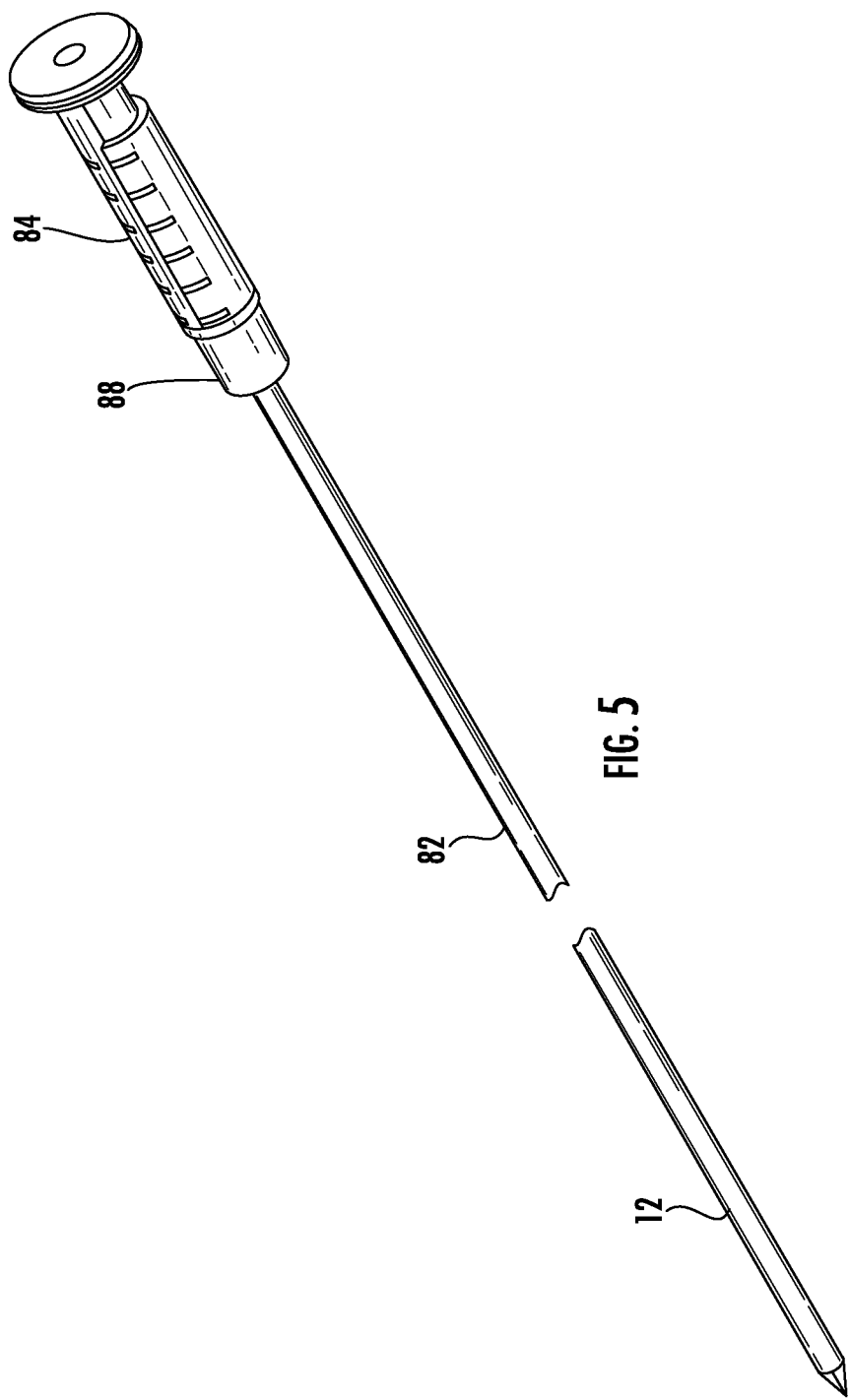
FIG. 5 is a partial view of one embodiment of the guide wire chuck and anvil in cooperation with a guide wire.

FIGS. 1-5, which are now referenced, illustrate one embodiment of the present invention and one manner in which it may be assembled. Like reference numerals refer to like components in the various figures. FIGS. 1-5 illustrate a surgical tool 100 for operation of a driving tool 10, a guide wire 12 and a bone screw 14, for example a pedicle screw, (FIG. 4). By way of example only, while placing bone screws through a pedicle (which is a small generally tubular structure connecting posterior elements of a vertebra to the vertebral body), it is critical to ensure the bone screw 14 is contained within the pedicle and does not breach the outer pedicle wall. Since the pedicle is surrounded by delicate nerve tissue, a breach can have serious consequences for the patient, ranging from mild pain to paralysis. One way to mitigate the risk of a pedicle breach during screw placement (including preparation for screw placement, such as pilot hole formation and tapping) is to determine the angular orientation of the pedicle, and thereafter advance the necessary instruments, guide wires and screws along the determined trajectory. By orienting the surgical access components along the pedicle trajectory with a guide wire, the surgical instruments and pedicle screws may be simply and efficiently advanced along the same trajectory, and thus avoid a breach.

Thus, in spinal surgery, before the pilot hole is formed with the guide wire 12, the desired angular trajectory must first be determined. Preoperative superior views utilizing AP fluoroscopy, MRI or CAT scan imaging device(s) are used to determine the trajectory once the surgical tool 100, in combination with the driving tool 10, bone screw 14 and guide wire 12, has been placed at the anatomical site for which the surgery is to be conducted. C-arm fluoroscopes are used extensively during many surgical procedures. During spinal surgery, for example, the C-arm is used frequently to help locate specific structures of the spine, to direct the positioning of surgical instruments and/or instrumentation, and to verify the proper alignment and height of vertebra, among other uses. Imaging devices, such as the C-arm, are typically provided with a scale (not shown) indicating the orientation of the radiography beam with respect to the patient and thus, in this example, the surgical tool 100, in combination with the driving tool 10, bone screw 14 and guide wire 12.

FIGS. 1-5, which are now referenced, illustrate one embodiment of the present invention and the manner in which it is constructed. In general, the figures illustrate a surgical tool 100 for creating a precise pilot bore using a guide wire 12 in a bone structure. The surgical tool 100 can further insert a bone screw 14 into the pilot bore without removal of the tool from the surgical site. The surgical tool 100 comprises a substantially rigid cannulated hand grip 16 including a first end 18 and a second end 20, the first end 18 including a quick release chuck 22 for securing to a driving tool 10, the second end 20 including a threaded barrel 26; the threaded barrel cooperating with a threaded jack 56. The threaded jack 56 includes an inner bore 27 for housing a slide assembly 24. The hand grip 16 is secured to the barrel 26 in a manner that prevents rotation between the two. The hand grip 16 may be fixed to the barrel 26 by various means, which include overmolding, or can be detachably removable. In embodiments where the hand grip 16 is detachably removable, the hand grip 16 may include adhesive, keyways, press fits, serrations or the like, which allow the hand grip 16 to adhere to the barrel 26 to prevent rotation between the hand grip 16 and the barrel 26 during operation. The quick release chuck 22 is operated by pressing the face plate 28 into the hand grip 16, depressing spring member 30 to allow the locking balls 32 to sufficiently retract to allow a driving tool 10 to be inserted or removed. Release of the face plate 28 allows the spring member 30 to force the face plate 28 outwardly, causing the locking balls 32 to retract inwardly to engage a ring or other indentions in the driving tool 10, preventing it from pulling out of the surgical tool 100. The quick release chuck 22 includes an inner sleeve 40 which includes the ramp surfaces 41 for the locking balls 32. The inner sleeve 40 is also constructed to contain the spring member 30, while guiding the face plate 28. The inner surface 34 of the quick release chuck 22 and the outer surface 36 of the driving tool 10 are provided with intermeshing, preferably conjugate shapes, which allow the surgical tool 100 to rotate the driving tool 10 in either direction. The distal end 36 of the driving tool 10 includes a shaped driver 38, which is constructed to cooperate with a female cavity in a bone screw 14 to allow the screw to be rotated into a bone. The driving tool 10 includes a bore extending along the longitudinal axis of the driving tool 10 for passage of a guide wire 12, biopsy needle (not shown), or the like.

Referring generally to the figures, and more specifically to FIG. 3, the barrel 26 is generally a tubular member having an enlarged head 42. Internal threads 43 are provided to cooperate with jack member 56. Adjustment of the jack member 56 provides a means to adjust and control the amount of travel provided to the slide assembly 24, which allows the guide wire 12 to travel through the hand grip 16, barrel 26, and driving tool 10 a predetermined distance. Adjustment of the jack member 56 changes the length of the surgical tool 100. In this manner, a guide wire 12 or needle of a predetermined length can be utilized to provide the surgeon with a guide of the depth the guide wire or needle will pass through the surgical tool 100. Pedicle screws are provided in predetermined lengths, thus the distance that the guide wire will pass through the surgical tool 100 and the screw 14 can also be determined prior to or during the surgery. Spacer tools 53 of predetermined length may be utilized to allow the surgeon to quickly establish the length the guide wire 12 will extend through the surgical tool 100. The spacer tools 53 may be U-shaped, or otherwise shaped, to allow the surgical tool 100 to be placed between the bottom surface 49 of the jack member head portion 51 and the rear surface 47 of the barrel 26. The jack member 56 is constructed to allow rotation of the slide assembly 24 during traversal of the slide assembly 24 within the jack member 56. The construction also allows the jack member 56 to rotate without rotation of the guide wire 12 when retracting the guide wire 12 from a bone.

Referring to FIG. 3, the slide assembly 24 is generally constructed and arranged to control the sliding travel distance of the guide wire 12 within the surgical tool assembly 100. The slide assembly 24 includes a slide head 64, stem portion 66, and wire lock assembly 72. The slide head 64 includes a transverse bore 70 sized and shaped to include a wire lock assembly 72 to secure the guide wire 12 in place within the slide assembly 24. The transverse bore 70 includes a spring 60 and shoe 61 to cooperate with the outer surface of the guide wire 12 to position and retain the guide wire 12. The guide wire 12 may include a head portion 62 having a shoulder 80 to provide a positive stop for the guide wire 12 within the slide assembly 24. The slide assembly 24 is sized to fit within the jack member 56 for sliding movement between the two. The internal threads 43 of the barrel 26 cooperate with the jack member 56, which controls the amount the slide assembly 24 will travel before the guide wire 12 extends through the distal end of the surgical tool 100 or the surgical tool 100 and the pedicle screw 14. The jack member 56 also provides the surgeon with the ability to withdraw the guide wire 12 from bone and from a bone screw 14 by rotation of the jack member 56. This construction also allows the surgeon to drive the guide wire 12 deeper into the bone if it is determined that it needs to be further moved after being set a first time by resetting the jack member 56. The guide wire 12 may be solid or cannulated; and may include any number of tips desirable for penetrating bone. It should also be noted that indicia 25 (FIG. 1) may be included on the barrel 26, slide assembly 24, or jack member 56 to assist the surgeon in controlling the movement of the guide wire 12. In some embodiments, the indicia may be embossed, printed, embedded or otherwise imprinted on a sticker or the like. In other embodiments, the indicia are etched or electro-plated into the hand grip 16. In some embodiments, the hand grip 16 may include a cutout region for accommodating indicia for depth.

One method of operation includes placing a bone screw 14 on the distal end 36 of driving tool 10. The wire lock is secured in the slide assembly 24 with the wire lock assembly 72, having the approximate amount of guide wire 12 extending outwardly therefrom. The guide wire 12 is slid through the slide assembly 24, depressing the wire lock assembly 72, allowing the wire lock assembly 72 to be locked into the slide assembly 24. The slide assembly 24 can then be inserted into the jack member 56, the guide wire 12 extending through the driving tool 10 and bone screw 14. Travel of the guide wire 12, and thus the amount that the guide wire 12 is allowed to extend through the bone screw 14, is adjusted by rotation of the jack member 56. The guide wire 12 can then be retracted to not extend through the bone screw 14. The bone screw 14 can be positioned as desired on the bone, and the slide assembly 24 impacted with a hammer or the like to drive the guide wire 12 into position. The guide wire 12 may be retracted for insertion of the bone screw 14, or be left in place while the screw 14 is inserted into the bone. The screw jack 56 can be utilized to retract the guide wire 12 in either scenario.

It should be noted that, while not illustrated, the present device 100 may be utilized for numerous orthopedic procedures that require precision and guidance. While not limited to the following list, such procedures may include other instruments such as drills, bone pins, hip, knee and shoulder replacements, as well as other surgical implantations where the surgeon desires to control the depth the tool is allowed to penetrate the bone. The device 100 may also be applicable for biopsies of tissue, particularly for small tumors and the like where depth of the biopsy needle must be closely controlled. The present device 100 may be used in parallel with devices, such as a drill, to control trajectory and depth of the drill.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A surgical guidance device and a guidewire for creating a pilot bore using the guide wire into a bone structure comprising:
  a cannulated hand grip including a first end and a second end, the first end including a driving tool for rotation of a bone screw, said second end including an internally threaded barrel, said threaded barrel cooperating with a threaded jack, said threaded jack includes an inner bore for housing a slide assembly, said slide assembly generally constructed and arranged to control the sliding travel distance of a guide wire within the surgical guidance device, said slide assembly includes a slide head for limiting forward sliding movement of a stem portion of said slide assembly within said threaded jack, said slide head includes a transverse bore sized and shaped to include a wire lock assembly to secure said guide wire in place within said slide assembly, said slide assembly sized to fit within said jack member for sliding movement between the two, said internal threads of said barrel cooperating with said jack member to control the distance said slide assembly will travel before said guide wire extends through a distal end of said surgical guidance device, said guide wire including a predetermined length, said threaded jack including indicia, whereby a surgeon may preset the distance that said guide wire will extend through the distal end of said surgical guidance device.

2. The surgical guidance device of claim 1 wherein said guide wire is a cannulated needle.

3. The surgical guidance device of claim 1 including at least one spacer tool adapted for insertion between a portion of said internally threaded barrel and a portion of said threaded jack for establishing the length said guide wire will extend through said surgical guidance device.

4. The surgical guidance device of claim 1 wherein said barrel is a tubular member having an enlarged head, said enlarged head forming the second end of said cannulated grip.

5. The surgical guidance device of claim 1 wherein said first end of said cannulated hand grip includes a quick release chuck for securing said cannulated hand grip to said driving tool.

6. The surgical guidance device of claim 1 wherein said driving tool is constructed and arranged for locating a pedicle screw along the guidewire, said pedicle screw cannulated to allow said guide wire to pass through said pedicle screw, whereby said pedicle screw is insertable into a bone along a trajectory created by said guide wire.

7. The surgical guidance device of claim 1 wherein said jack member also provides the surgeon with the ability to withdraw the guide wire from bone and from a bone screw by rotation of the jack member with respect to the cannulated hand grip.

8. The surgical guidance device of claim 1 wherein a distal end of said driving tool includes a shaped driver which is constructed to cooperate with a female cavity in a bone screw to allow said bone screw to be rotated into a bone.

9. The surgical guidance device of claim 8 wherein said driving tool includes a bore extending along the longitudinal axis of said driving tool for passage of a guide wire.

10. The surgical guidance device of claim 1 wherein said hand grip is secured to said barrel in a manner that prevents rotation between the two.

11. The surgical guidance device for creating a pilot bore in a bone structure comprising:
a cannulated hand grip including a first end and a second end, the first end including a driving tool for rotation of a bone screw, said second end including an internally threaded barrel, said threaded barrel cooperating with a threaded jack, said threaded jack includes an inner bore for housing a slide assembly, said slide assembly generally constructed and arranged to control the sliding travel distance of a guide wire within the surgical guidance device, said slide assembly includes a slide head for limiting forward sliding movement of a stem portion of said slide assembly within said threaded jack, said slide head includes a transverse bore sized and shaped to include a wire lock assembly to secure said guide wire in place within said slide assembly, said slide assembly sized to fit within said jack member for sliding movement between the two, said internal threads of said barrel cooperating with said jack member to control the distance said slide assembly will travel before said guide wire extends through a distal end of said surgical guidance device, at least one spacer tool adapted for insertion between a portion of said internally threaded barrel and a portion of said threaded jack for establishing the length said guide wire will extend through said surgical guidance device.

12. The surgical guidance device of claim 11 wherein said jack member is constructed and arranged to withdraw the guide wire from bone and from a bone screw by rotation of the jack member with respect to the cannulated hand grip.

13. The surgical guidance device of claim 11 wherein a distal end of said driving tool includes a shaped driver which is constructed to cooperate with a female cavity in a bone screw to allow said bone screw to be rotated into a bone.

* * * * *